United States Patent
Patel et al.

(10) Patent No.: US 10,231,977 B2
(45) Date of Patent: *Mar. 19, 2019

(54) TRANSDERMAL DRUG DELIVERY SYSTEMS FOR LEVONORGESTREL AND ETHINYL ESTRADIOL

(71) Applicant: Noven Pharmaceuticals, Inc., Miami, FL (US)

(72) Inventors: Prashant Patel, Miami, FL (US); Viet Nguyen, Miami, FL (US); Jun Liao, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/069,425

(22) Filed: Mar. 14, 2016

(65) Prior Publication Data

US 2016/0296535 A1   Oct. 13, 2016

Related U.S. Application Data

(63) Continuation of application No. 14/141,935, filed on Dec. 27, 2013, now Pat. No. 9,314,470.

(60) Provisional application No. 61/747,013, filed on Dec. 28, 2012.

(51) Int. Cl.
| | | |
|---|---|---|
| A61K 31/565 | (2006.01) |
| A61K 9/70 | (2006.01) |
| A61K 47/10 | (2017.01) |
| A61K 47/14 | (2017.01) |
| A61K 31/567 | (2006.01) |

(52) U.S. Cl.
CPC .......... *A61K 31/567* (2013.01); *A61K 9/7061* (2013.01); *A61K 31/565* (2013.01); *A61K 47/10* (2013.01); *A61K 47/14* (2013.01)

(58) Field of Classification Search
CPC .. A61K 9/7061; A61K 9/7053; A61K 31/565; A61K 31/567
See application file for complete search history.

(56) References Cited

U.S. PATENT DOCUMENTS

| | | | |
|---|---|---|---|
| 4,863,738 A * | 9/1989 | Taskovich | A61K 9/0014 424/449 |
| 5,053,227 A | 10/1991 | Chiang et al. | |
| 5,234,957 A | 8/1993 | Mantelle | |
| 5,332,576 A | 7/1994 | Mantelle et al. | |
| 5,446,070 A | 8/1995 | Mantelle | |
| 5,719,197 A | 2/1998 | Kanios et al. | |
| 5,958,446 A | 9/1999 | Miranda et al. | |
| 6,024,974 A | 2/2000 | Li | |
| 6,024,976 A | 2/2000 | Miranda | |
| 6,210,705 B1 | 4/2001 | Mantelle et al. | |
| 6,235,306 B1 | 5/2001 | Miranda et al. | |
| 6,316,022 B1 | 11/2001 | Mantelle et al. | |
| 6,348,211 B1 | 2/2002 | Mantelle et al. | |
| 7,045,145 B1 * | 5/2006 | Chien | A61K 9/0014 424/443 |
| 7,846,916 B2 | 12/2010 | Houze | |
| 7,867,986 B2 | 1/2011 | Houze | |
| 7,879,831 B2 | 2/2011 | Houze | |
| 7,989,496 B2 | 8/2011 | Hartwig et al. | |
| 7,993,671 B2 | 8/2011 | Mantelle et al. | |
| 8,153,151 B2 | 4/2012 | Houze | |
| 8,187,628 B2 | 5/2012 | Houze | |
| 8,216,606 B2 | 7/2012 | Houze | |
| 8,231,906 B2 | 7/2012 | Mantelle | |
| 8,246,976 B2 | 8/2012 | Nguyen | |
| 8,277,838 B2 | 10/2012 | Nguyen | |
| 8,337,884 B2 | 12/2012 | Mantelle et al. | |
| 8,343,538 B2 | 1/2013 | Kanios et al. | |
| 8,632,802 B2 | 1/2014 | Kanios | |
| 8,703,175 B2 | 4/2014 | Kanios et al. | |
| 8,715,723 B2 | 5/2014 | Kanios et al. | |
| 8,784,874 B2 | 7/2014 | Strauss | |
| 8,784,877 B2 | 7/2014 | Houze et al. | |
| 8,852,628 B1 | 10/2014 | Houze et al. | |
| 9,314,470 B2 | 4/2016 | Patel et al. | |
| 2002/0004065 A1 | 1/2002 | Kanios | |
| 2004/0053901 A1 | 3/2004 | Chien et al. | |
| 2009/0098191 A1 * | 4/2009 | Anderson | A61K 9/7053 424/443 |
| 2011/0129535 A1 | 6/2011 | Mantelle | |
| 2011/0160245 A1 | 6/2011 | Mantelle et al. | |
| 2011/0288124 A1 | 11/2011 | Mantelle et al. | |
| 2013/0156815 A1 | 6/2013 | Mantelle | |
| 2013/0317461 A1 | 11/2013 | Kanios et al. | |
| 2013/0324575 A1 | 12/2013 | Mantelle et al. | |

(Continued)

FOREIGN PATENT DOCUMENTS

| | | |
|---|---|---|
| JP | 01-165529 A | 6/1989 |
| JP | 2007-217328 A | 8/2017 |

(Continued)

OTHER PUBLICATIONS

International Search Report dated Apr. 14, 2014 in application No. PCT/US2013/077932.
Office Action dated Jul. 30, 2015 in U.S. Appl. No. 14/141,935 (now U.S. Pat. No. 9,314,470).
Notice of Allowance dated Dec. 15, 2015 in U.S. Appl. No. 14/141,935 (now U.S. Pat. No. 9,314,470).
Office Action dated Aug. 22, 2017 in U.S. Appl. No. 15/200,397 (US 2017-0000745).
Office Action dated Mar. 5, 2018 in U.S. Appl. No. 15/200,397 (US 2017-0000745).

(Continued)

*Primary Examiner* — H. Sarah Park
(74) *Attorney, Agent, or Firm* — Foley & Lardner LLP (57) ABSTRACT

Described are transdermal drug delivery systems for the transdermal administration of levonorgestrel and ethinyl estradiol, comprising an acrylic polymer matrix. Methods of making and using such systems also are described.

11 Claims, 3 Drawing Sheets

(56) References Cited

U.S. PATENT DOCUMENTS

| | | |
|---|---|---|
| 2014/0105979 A1 | 4/2014 | Liao et al. |
| 2014/0121611 A1 | 5/2014 | Lambert et al. |
| 2014/0178459 A1 | 6/2014 | Kisak et al. |
| 2014/0179739 A1 | 6/2014 | Mantelle et al. |
| 2014/0182597 A1 | 7/2014 | Patel et al. |
| 2014/0186424 A1 | 7/2014 | Kulakofsky et al. |
| 2014/0188056 A1 | 7/2014 | Mori et al. |
| 2014/0200530 A1 | 7/2014 | Mantelle |
| 2014/0243764 A1 | 8/2014 | Kanios et al. |
| 2014/0248330 A1 | 9/2014 | Kanios |
| 2014/0271792 A1 | 9/2014 | Liao et al. |
| 2014/0271865 A1 | 9/2014 | Lambert et al. |
| 2014/0276478 A1 | 9/2014 | Liao et al. |
| 2014/0276479 A1 | 9/2014 | Nguyen et al. |
| 2014/0276483 A1 | 9/2014 | Liao et al. |
| 2014/0288038 A1 | 9/2014 | Kanios et al. |
| 2014/0322298 A1 | 10/2014 | Nguyen et al. |
| 2017/0000745 A1 | 1/2017 | Kulakofsky et al. |

FOREIGN PATENT DOCUMENTS

| | | |
|---|---|---|
| WO | WO 01/37770 A1 | 5/2001 |
| WO | WO 2009/009649 A1 | 1/2009 |
| WO | WO-2011/118683 A1 | 9/2011 |

OTHER PUBLICATIONS

Partial translation of Office Action dated Mar. 14, 2018 in Japanese application No. 2015-550784.
Terahara, "Improvement of Gastrointestinal and Transmucosal Absorption of Poorly Absorbable Drugs and Development of Novel Dosage Forms of These Drugs", The First Impression (2012), pp. 257-264.

* cited by examiner

TRANSDERMAL DRUG DELIVERY SYSTEMS FOR LEVONORGESTREL AND ETHINYL ESTRADIOL

CROSS REFERENCE TO RELATED APPLICATIONS

This application is a continuation of U.S. patent application Ser. No. 14/141,935, filed Dec. 27, 2013, and claims the benefit under 35 USC § 119(e) to U.S. provisional application 61/747,013, filed Dec. 28, 2012, the entire contents of which are incorporated herein by reference in their entirety.

FIELD OF THE INVENTION

Described herein are compositions and methods for the transdermal delivery of levonorgestrel and ethinyl estradiol. The compositions and methods are useful, for example, as contraceptives.

BACKGROUND

Transdermal delivery systems (adhesive patches) as dosage forms have been the subject of a vast number of patent applications over the last 25 years, yielding many patents but few commercial products in comparison. To those working in the field, the relatively small number of commercial products is not surprising. Although regulatory, economic, and market hurdles play a role in limiting the number of products on the market, the task of developing a transdermal delivery system that achieves desired physical and pharmacokinetic parameters to satisfy physician and patient demand is more daunting. Parameters to be considered during commercial product development may include drug solubility, drug stability (e.g., as may arise from interaction with other component materials and/or the environment), delivery of a therapeutic amount of drug at a desired delivery rate over the intended duration of use, adequate adhesion at the anatomical site of application, integrity (e.g., minimal curling, wrinkling, delaminating and slippage) with minimal discomfort, irritation and sensitization both during use and during and after removal, and minimal residual adhesive (or other components) after removal. Size also may be important from a manufacturing and patient viewpoint, and appearance may be important from a patient viewpoint. These factors become even more complicated when more than one drug is being formulated.

This invention relates generally to transdermal drug delivery systems, and more particularly, to transdermal drug delivery systems for the delivery of levonorgestrel and ethinyl estradiol.

U.S. Pat. No. 7,045,145 is directed to a transdermal delivery system comprising a backing layer, and an adhesive polymer matrix affixed to the backing layer, wherein the adhesive polymer matrix is formulated by combining, on a weight percentage basis: (a) from about 0% to about 10% of a humectant/plasticizer; (b) from about 20% to about 70% of an adhesive copolymer; (c) from about 10% to about 60% percent of a combination of skin permeation enhancing agents which is a mixture comprising dimethyl sulfoxide, a fatty (C8-C20) alcohol ester of lactic acid, a lower (C1-C4) alkyl ester of lactic acid and capric acid present in ratio ranging from about 2:1:1:0.8 to about 6:1:1:0.8, respectively; (d) a progestin hormone; and (e) an estrogen hormone.

U.S. Pat. No. 7,384,650 is directed to a transdermal hormone delivery system comprising a backing layer and an adhesive polymer matrix affixed to the backing layer, wherein the adhesive polymer matrix comprises: (a) an adhesive polymer; (b) a humectant; (c) a combination of skin permeation enhancing agents consisting essentially of, on a final percentage by weight of the adhesive polymer matrix after fabrication of the system, from about 4% to about 12% dimethyl sulfoxide; from about 4.2% to about 12.6% a fatty (C8-C20) alcohol ester of lactic acid; from about 0.7% to about 2.3% lower (C1-C4) alkyl ester of lactic acid; and from about 3% to about 9% capric acid; (d) a progestin; and (e) an estrogen.

U.S. Pat. No. 8,221,785 is directed to a contraceptive delivery system comprising a backing layer and an adhesive polymer matrix affixed to the backing layer, wherein the adhesive polymer matrix comprises: (a) an adhesive polymer comprising a polyacrylate copolymer; (b) a humectant comprising polyvinylpyrrolidone; (c) a combination of skin permeation enhancing agents consisting essentially of, on a final percentage by weight of the adhesive polymer matrix after fabrication of the system, from about 4% to about 12% dimethyl sulfoxide; from about 4.2% to about 12.6% a fatty (C8-C20) alcohol ester of lactic acid; from about 0.7% to about 2.3% lower (C1-C4) alkyl ester of lactic acid; and from about 3% to about 9% capric acid; (d) levonorgestrel; and (e) ethinyl estradiol or 17 beta-estradiol.

U.S. Pat. No. 5,770,219 is directed to a drug-containing matrix for use in a transdermal drug delivery device for administering at least one estrogen to an area of skin or mucosa comprising the estrogen dispersed in a body of a pressure sensitive adhesive, said pressure-sensitive adhesive comprising an acetate acrylate copolymer and polyvinylpyrrolidone, said matrix being essentially free of a skin permeation enhancer. In some embodiments, the matrix further comprises levonorgestrel.

Nevertheless, the transdermal delivery of levonorgestrel and ethinyl estradiol continues to present challenges, and currently there is no commercial transdermal combination product on the market. Some of the challenges presented by this particular drug combination include the high delivery rate of levonorgestrel and its impact on patch size; the undesired crystallization of levonorgestrel in the polymer matrix; and the difficulty of formulating a composition that can achieve sustained drug delivery (e.g., at therapeutic levels) over a period of time of 7 days.

Thus, there remains a need for transdermal drug delivery systems designed for the delivery of specific drugs and drug combinations, such as levonorgestrel and ethinyl estradiol.

SUMMARY

In accordance with some embodiments, there are provided transdermal drug delivery systems for the transdermal delivery of levonorgestrel and ethinyl estradiol in the form of a flexible finite system for topical application, comprising a polymer matrix comprising levonorgestrel, ethinyl estradiol, and an acrylic polymer, wherein the acrylic polymer may comprise a hydroxy functional acrylic polymer. In some embodiments, the polymer matrix is substantially free of or free of polyvinylpyrrolidone (PVP) and polyvinylpyrrolidone/vinylacetate (PVP/VA).

In some embodiments, the transdermal drug delivery system further comprises a penetration enhancer. In specific embodiments, the polymer matrix comprises 0.1 to 3% levonorgestrel; 0.1 to 5% ethinyl estradiol; 5 to 20% penetration enhancer, and the balance acrylic polymer. In any embodiments, the penetration enhancer may be glyceryl monooleate, dipropylene glycol, or mixtures thereof.

In any embodiments, the transdermal drug delivery system may comprise an amount of levonorgestrel sufficient to achieve sustained delivery of levonorgestrel over a period of time of at least 3 days, at least 4 days, or at least 7 days.

In any embodiments, the transdermal drug delivery system may comprise an amount of ethinyl estradiol sufficient to achieve sustained delivery of ethinyl estradiol over a period of time of at least 3 days, at least 4 days, or at least 7 days.

In any embodiments, the transdermal drug delivery system may further comprise a backing layer and/or a release liner.

Also provided are methods of transdermally delivering levonorgestrel and ethinyl estradiol comprising applying a transdermal drug delivery system as described herein to the skin or mucosa of a subject in need thereof. In some embodiments, the subject is a human female subject. In some embodiments, the method is for contraception. In some embodiments, the transdermal drug delivery system is applied for a duration of up to 7 days.

Also provided are methods of preparing a transdermal drug delivery system comprising levonorgestrel and ethinyl estradiol as described herein, comprising preparing a polymer matrix as described herein, comprising levonorgestrel, ethinyl estradiol, and an acrylic polymer.

DETAILED DESCRIPTION

In accordance with some embodiments, the present invention provides transdermal drug delivery systems for the transdermal delivery of levonorgestrel and ethinyl estradiol. In specific embodiments, the systems exhibit desired pharmacokinetic properties, such as by being capable of formulation for use over a 7 day period, and/or exhibit desired stability characteristics, such as reduced or minimized crystallization of levonorgestrel.

The present inventors surprisingly discovered that levonorgestrel and ethinyl estradiol could be formulated together in a polymer matrix without the need for humectant such as polyvinylpyrollidone (PVP) or polyvinylpyrollidone/vinylacetate (PVP/VA). The present inventors also surprisingly discovered that acrylic polymers comprising hydroxy functional groups (such as hydroxyl functional group containing vinyl acetates) are particularly suitable for formulating levonorgestrel for sustained delivery over an extended period of time (such as 7 days). The present inventors also surprisingly discovered that each of dipropylene glycol (DPG) and glyceryl monooleate (GMO) alone or in combination are effective enhancers for levonorgestrel.

In accordance with some aspects, there are provided transdermal drug delivery systems and methods for the transdermal delivery of levonorgestrel and ethinyl estradiol.

In specific embodiments, the systems exhibit sustained delivery of levonorgestrel and ethinyl estradiol over an extended period of time, such as for at least 3 days, 4 days, 7 days, or longer.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein generally means that the described composition (e.g., transdermal drug delivery system, polymer matrix, etc.) comprises less than about 5%, less than about 3%, or less than about 1% by weight, based on the total weight of the composition at issue, of the excluded component. The phrase "free of" as used herein means that the described composition (e.g., polymer matrix, etc.) is formulated without adding the excluded component(s) as an intended component, although trace amounts may be present in other components or as a by-product or contaminant, such that the composition comprises at most only trace amounts of the excluded component(s).

As used herein "subject" denotes any animal in need of drug therapy, including humans. For example, a subject may be suffering from or at risk of developing a condition that can be treated or prevented with levonorgestrel and ethinyl estradiol, or may be taking levonorgestrel and ethinyl estradiol for health maintenance purposes. In specific embodiments, the subject is a female subject taking levonorgestrel and ethinyl estradiol for contraceptive purposes.

As used herein, the phrases "therapeutically effective amount" and "therapeutic level" mean that drug dosage or plasma concentration in a subject, respectively, that provides the specific pharmacological response for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As used herein, "active surface area" means the surface area of the drug-containing layer of the transdermal drug delivery system.

As used herein, "coat weight" refers to the weight of the drug-containing layer per unit area of the active surface area of the transdermal drug delivery system.

As used herein, "flux" (also called "permeation rate") is defined as the absorption of a drug through skin or mucosal tissue, and is described by Fick's first law of diffusion:

$$J=-D(dCm/dx)$$

where J is the flux in g/cm2/sec, D is the diffusion coefficient of the drug through the skin or mucosa in cm2/sec and dCm/dx is the concentration gradient of the drug across the skin or mucosa.

As used herein, the term "transdermal" refers to delivery, administration or application of a drug by means of direct contact with skin or mucosa. Such delivery, administration or application is also known as dermal, percutaneous, transmucosal and buccal. As used herein, "dermal" includes skin and mucosa, which includes oral, buccal, nasal, rectal and vaginal mucosa.

As used herein, "transdermal drug delivery system" refers to a system (e.g., a device) comprising a composition that releases drug upon application to the skin (or any other surface noted above). A transdermal drug delivery system may comprise a drug-containing layer, and, optionally, a backing layer and/or a release liner layer. In some embodiments, the transdermal drug delivery system is a substantially non-aqueous, solid form, capable of conforming to the surface with which it comes into contact, and capable of maintaining such contact so as to facilitate topical application without adverse physiological response, and without being appreciably decomposed by aqueous contact during topical application to a subject. Many such systems are known in the art and commercially available, such as transdermal drug delivery patches. As described below, in one embodiment, the transdermal drug delivery system comprises a drug-containing polymer matrix that comprises a pressure-sensitive adhesive or bioadhesive, and is adopted for direct application to a user's (e.g., a subject's) skin. In other embodiments, the polymer matrix is non-adhesive and may be provided with separate adhesion means (such as a separate adhesive layer) for application and adherence to the user's skin.

As used herein, "polymer matrix" refers to a polymer composition which contains one or more drugs. In some embodiments, the matrix comprises a pressure-sensitive adhesive polymer or a bioadhesive polymer. In other embodiments, the matrix does not comprise a pressure-sensitive adhesive or bioadhesive. As used herein, a polymer is an "adhesive" if it has the properties of an adhesive per se, or if it functions as an adhesive by the addition of tackifiers, plasticizers, crosslinking agents or other additives. Thus, in some embodiments, the polymer matrix comprises a pressure-sensitive adhesive polymer or a bioadhesive polymer, with drug dissolved or dispersed therein. The polymer matrix also may comprise tackifiers, plasticizers, crosslinking agents, enhancers, co-solvents, fillers, antioxidants, solubilizers, crystallization inhibitors, or other additives described herein. U.S. Pat. No. 6,024,976 describes polymer blends that are useful in accordance with the transdermal systems described herein. The entire contents of U.S. Pat. No. 6,024,976 is incorporated herein by reference.

As used herein, the term "pressure-sensitive adhesive" refers to a viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives.

The term pressure-sensitive adhesive also includes mixtures of different polymers and mixtures of polymers, such as polyisobutylenes (PIB), of different molecular weights, wherein each resultant mixture is a pressure-sensitive adhesive. In the last case, the polymers of lower molecular weight in the mixture are not considered to be "tackifiers," said term being reserved for additives which differ other than in molecular weight from the polymers to which they are added.

In some embodiments, the polymer matrix is a pressure-sensitive adhesive at room temperature and has other desirable characteristics for adhesives used in the transdermal drug delivery art. Such characteristics include good adherence to skin, ability to be peeled or otherwise removed without substantial trauma to the skin, retention of tack with aging, etc. In some embodiments, the polymer matrix has a glass transition temperature (Tg), measured using a differential scanning calorimeter, of between about −70° C. and 0° C.

As used herein, the term "rubber-based pressure-sensitive adhesive" refers to a viscoelastic material which has the properties of a pressure-sensitive adhesive and which contains at least one natural or synthetic elastomeric polymer.

In some embodiments, the transdermal drug delivery system includes one or more additional layers, such as one or more additional polymer matrix layers, or one or more adhesive layers that adhere the transdermal drug delivery system to the user's skin. In other embodiments, the transdermal drug delivery system is monolithic, meaning that it comprises a single polymer matrix layer comprising a pressure-sensitive adhesive or bioadhesive with drug dissolved or dispersed therein, and no rate-controlling membrane.

The transdermal drug delivery system also may include a drug impermeable backing layer or film. In some embodiments, the backing layer is adjacent one face of the polymer matrix layer. When present, the backing layer protects the polymer matrix layer (and any other layers present) from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1000 micrometers. For example, 3M's Scotch Pak™ 1012 or 9732 backing material (a polyester film with an ethylene vinyl acetate copolymer heat seal layer) is useful in the transdermal drug delivery systems described herein.

The transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include the commercially available products of Dow Corning Corporation designated Bio-Release® liner and Syl-off® 7610 (both silicone-based) and 3M's 1020, 1022, 9744, 9748 and 9749 Scotchpak™ (fluoropolymer coated polyester films).

The transdermal drug delivery system may be packaged or provided in a package, such as a pouchstock material used in the prior art for transdermal drug delivery systems in general. For example, DuPont's Surlyn® can be used in a pouchstock material.

As used herein, a "monolithic" transdermal drug delivery system may include a backing layer and/or release liner, and may be provided in a package.

Polymer Matrix

In accordance with some embodiments, the compositions described herein comprise a polymer matrix that comprises, consists essentially of, or consists of levonorgestrel, ethinyl estradiol, at least one acrylic polymer, and, optionally, at least one penetration enhancer. In this context, the phrase "consists essentially of" means that the polymer matrix is substantially free of other polymer components (e.g., substantially free of polymers other than one or more acrylic polymers) although it may include other excipients known to be useful in transdermal compositions (such as tackifiers, plasticizers, crosslinking agents or other excipients known in the art) as long as those other excipients do not degrade the physical and/or pharmacokinetic properties of the compositions to pharmaceutically unacceptable levels.

In some embodiments, the compositions described herein are free of or are substantially free of a humectant, such as polyvinylpyrrolidone (PVP) and polyvinylpyrrolidone/vinylacetate (PVP/VA), as used in U.S. Pat. No. 7,045,145. As noted above, the present inventors surprisingly discovered that stable compositions could be prepared without PVP or PVP/VA. While PVP typically is believed to suppress crystal formation in transdermal drug delivery systems, the inventors surprisingly discovered that levonorgestrel formulations that are substantially free of or free of PVP exhibit less crystallization than levonorgestrel formulations that comprise PVP.

In some embodiments, the polymer matrix comprises (on a weight % basis) about 0.1-3% levonorgestrel, about 0.1-5% ethinyl estradiol, about 5-20% penetration enhancer(s), and the balance acrylic polymer(s).

Levonorgestrel

Levonorgestrel is a synthetic progestogen. It is an enantiomer of the chiral compound 13-ethyl-17-ethynyl-17-hydroxy-1,2,6,7,8,9,10,11,12,13,14,15,16,17-tetradecahydrocyclopenta[a] phenanthren-3-one.

Ethinyl Estradiol

Ethinyl estradiol is an estrogen with the chemical name 19-nor-17α-pregna-1,3,5(10)-trien-20-yne-3,17-diol.

The amount of levonorgestrel and ethinyl estradiol to be incorporated in the polymer matrix varies depending on the desired therapeutic effect, and the time span for which the system is to provide therapy. For most drugs, the passage of the drugs through the skin will be the rate-limiting step in delivery. A minimum amount of drug in the system is selected based on the amount of drug which passes through the skin in the time span for which the system is to provide therapy. In some embodiments, a system for the transdermal delivery of levonorgestrel and ethinyl estradiolis used over a period of about 1 day, about 3 days, about 7 days, or longer. Thus, in one embodiment, the systems comprise an amount of drug (e.g., levonorgestrel and ethinyl estradiol) sufficient to deliver therapeutically effective amounts of drug over a period of from 1 day to 3 days, 7 days, or longer, including for 1 day, for 2 days, for 3 days, for 4 days, for 5 days, for 6 days, for 7 days, or for longer.

The inventors surprisingly discovered that the amount of ethinyl estradiol can be selected and controlled to select and control the transdermal delivery of ethinyl estradiol without substantially impacting the transdermal delivery of levonorgestrel. That is, the flux of ethinyl estradiol can be increased by increasing the relative amount of ethinyl estradiol without substantially impacting the transdermal delivery of levonorgestrel.

In some embodiments, the polymer matrix comprises from about 0.1% to about 50%, including from about 1% to about 20%, such as from about 1% to about 10% by weight, of active agent. In some embodiments, the polymer matrix comprises from about 0.1% to about 25%, including from about 1% to about 10%, such as from about 1% to about 5% by weight, of levonorgestrel. In some embodiments, the polymer matrix comprises from about 0.1% to about 25%, including from about 1% to about 10%, such as from about 1% to about 5% by weight, of ethinyl estradiol.

In some embodiments, the polymer matrix comprises from about 0.1 to 3% or 0.1 to 5% by weight levonorgestrel. In some embodiments, the polymer matrix comprises from about 0.1 to 3% or 0.1 to 5% by weight ethinyl estradiol.

Acrylic Polymers

The term "acrylic polymer" is used here as in the art interchangeably with "polyacrylate," "polyacrylic polymer," and "acrylic adhesive." The acrylic-based polymers can be any of the homopolymers, copolymers, terpolymers, and the like of various acrylic acids or esters. In some embodiments, the acrylic-based polymers are adhesive polymers. In other embodiments, the acrylic-based polymers function as an adhesive by the addition of tackifiers, plasticizers, crosslinking agents or other additives.

The acrylic polymer can include copolymers, terpolymers and multipolymers. For example, the acrylic polymer can be any of the homopolymers, copolymers, terpolymers, and the like of various acrylic acids. In some embodiments, the amount and type of acrylic polymer is dependent on the amounts of levonorgestrel and ethinyl estradiol used.

Acrylic polymers useful in practicing the invention include polymers of one or more monomers of acrylic acids and other copolymerizable monomers. The acrylic polymers also include copolymers of alkyl acrylates and/or methacrylates and/or copolymerizable secondary monomers or monomers with functional groups. Combinations of acrylic-based polymers based on their functional groups is also contemplated. Acrylic-based polymers having functional groups include copolymers and terpolymers which contain, in addition to nonfunctional monomer units, further monomer units having free functional groups. The monomers can be monofunctional or polyfunctional. By varying the amount of each type of monomer added, the cohesive properties of the resulting acrylic polymer can be changed as is known in the art. In some embodiments, the acrylic polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid and methacrylic acid and alkyl acrylic or methacrylic esters such as methyl acrylate, ethyl acrylate, propyl acrylate, amyl acrylate, butyl acrylate, butyl methacrylate, hexyl acrylate, methyl methacrylate, hexyl methacrylate, heptyl acrylate, octyl acrylate, nonyl acrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, glycidyl acrylate, and corresponding methacrylic esters.

Non-functional acrylic-based polymers can include any acrylic based polymer having no or substantially no free functional groups.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

As used herein, "functional monomers or groups," are monomer units typically in acrylic-based polymers which have reactive chemical groups which modify the acrylic-based polymers directly or which provide sites for further reactions. Examples of functional groups include carboxyl, epoxy, hydroxyl, sulfoxyl, and amino groups. Acrylic-based polymers having functional groups contain, in addition to the nonfunctional monomer units described above, further monomer units having free functional groups. The monomers can be monofunctional or polyfunctional. These functional groups include carboxyl groups, hydroxy groups, amino groups, amido groups, epoxy groups, etc. Typical carboxyl functional monomers include acrylic acid, methacrylic acid, itaconic acid, maleic acid, and crotonic acid. Typical hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate. As noted above, in some embodiments, the acrylic polymer does not include such functional groups.

In some embodiments, the acrylic polymer includes hydroxy functional monomers. Such polymers generally exhibit good solubility for levonorgestrel, which allows sufficient loading of levonorgestrel for preparation of a system that achieves transdermal delivery of a therapeutically effective amount of active agent over an extended period of time, such as a period of at least 3 days, at least 4 days, or at least 7 days, or longer.

Further details and examples of acrylic adhesives which are suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, New York (1989); "Acrylic and Methacrylic Ester Polymers," *Polymer Science and Engineering*, Vol. 1, 2nd ed., pp 234-268, John Wiley & Sons, (1984); U.S. Pat. No. 4,390,520; and U.S. Pat. No. 4,994,267, all of which are expressly incorporated by reference in their entireties.

Suitable acrylic polymers also include pressure-sensitive adhesives which are commercially available, such as the acrylic-based adhesives sold under the trademarks DURO-TAK® by National Starch and Chemical Corporation, Bridgewater, N.J. (such as DURO-TAK® 87-2516, 87-2287, -4098, -2852, -2196, -2296, -2194, -2516, -2070, -2353, -2154, -2510, -9085, -9088 and 73-9301). Other suitable acrylic adhesives include those sold under the trademark EUDRAGIT® by Roehm Pharma GmbH, Darmstadt, Germany, those sold by Cytec Surface Specialties, St. Louis, Mo., under the trademarks GELVA® Multipolymer Solution (such as GELVA® 2480, 788, 737, 263, 1430, 1753, 1151, 2450, 2495, 3067, 3071, 3087 and 3235). For example, hydroxy functional adhesives with a reactive functional OH group in the polymeric chain, can be used. Non-limiting commercial examples of this type of adhesives include both GELVA® 737, 788, and 1151, and DURO-TAK® 87-2287, -4287, -2510 and -2516.

In some embodiments, the acrylic polymer constitutes up to 100% by weight of the polymer content of the polymer matrix, including 100%

Other Components

In one embodiment, the polymer matrix comprises a penetration enhancer. A "penetration enhancer" is an agent known to accelerate the delivery of the drug through the skin. These agents also have been referred to as accelerants, adjuvants, and sorption promoters, and are collectively referred to herein as "enhancers." This class of agents includes those with diverse mechanisms of action, including those which have the function of improving percutaneous absorption, for example, by changing the ability of the stratum corneum to retain moisture, softening the skin, improving the skin's permeability, acting as penetration assistants or hair-follicle openers or changing the state of the skin including the boundary layer.

Illustrative penetration enhancers include but are not limited to polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin which affect the ability of keratin to retain moisture; polar solvents such as dimethyidecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In one embodiment, the penetration enhancer is a glycol, such as dipropylene glycol, propylene glycol, butylene glycol or polyethylene glycol. In other embodiments, the penetration enhancer comprises glyceryl monooleate. In other embodiments, the penetration enhancer comprises a mixture of at least two penetration enhancers. For example, a penetration enhancer may comprise dipropylene glycol and glyceryl monooleate. As noted above, the inventors surprisingly discovered that each of dipropylene glycol and glyceryl monooleate alone or in combination are effective enhancers for levonorgestrel.

In some embodiments, a penetration enhancer is used in an amount up to about 30% by dry weight of the polymer matrix, including up to 30% by weight, up to about 20% by weight, including 20% by weight, or up to about 10% by weight, up to 10% by weight, or up to 5% by weight, including up to 5% by weight, based on the dry weight of the polymer matrix. In some embodiments, a penetration enhancer is used in an amount of from about 5% to about 20%, including about 10% by weight.

The polymer matrix may further comprise various thickeners, fillers, and other additives or components known for use in transdermal drug delivery systems.

As noted above, in embodiments where the polymer matrix comprises a pressure-sensitive adhesive or bioadhesive, the polymer matrix can serve as an adhesive portion of the system (e.g., a reservoir device), or can serve as one or more layers of a multi-layer system. Alternatively, a polymer matrix comprising a pressure-sensitive adhesive or bioadhesive with drug dissolved or dispersed therein can constitute a monolithic device. In embodiments where the polymer matrix does not comprise an adhesive, but instead, for example, comprises a polymeric drug reservoir, it can be used in combination with one or more adhesive layers, or with a surrounding adhesive portion, as is well known to those skilled in the art.

In some embodiments, the system consists essentially of the polymer matrix layer. By "consists essentially of the polymer matrix layer" means that the system does not contain any other layers that affect drug delivery, such as an additional rate-controlling polymer layer, rate-controlling membrane, or drug reservoir layer. It will be understood, however, that the system that consists essentially of the polymer matrix layer may comprise a backing layer and/or release liner.

The system may be of any shape or size suitable for transdermal application. The polymer matrices described herein may be prepared by methods known in the art. The polymer matrices can be formed into systems by methods known in the art. For example, the polymer matrix material can be applied to a backing layer and release liner by methods known in the art, and formed into sizes and shapes suitable for use. For example, after the polymer matrix is formed, it may be brought into contact with a support layer, such a releaser liner layer or backing layer, in any manner known to those of skill in the art. Such techniques include calender coating, hot melt coating, solution coating, etc.

For example, a polymer matrix can be prepared by blending the components of the polymer matrix, applying the matrix material to a support layer such as a backing layer or release liner, and removing any remaining solvents. The levonorgestrel and ethinyl estradiol can be added at any stage. In one embodiment, all polymer matrix components, including levonorgestrel and ethinyl estradiol, are blended together. In another embodiment, the polymer matrix components other than levonorgestrel and ethinyl estradiol are blended together, and then the levonorgestrel and ethinyl estradiol is dissolved or dispersed therein. The order of steps, amount of ingredients, and the amount and time of agitation or mixing can be determined and optimized by the skilled practitioner. An exemplary general method is as follows:

Appropriate amounts of polymer(s), levonorgestrel, ethinyl estradiol, enhancer(s), and organic solvent(s) (for example toluene, or ethyl acetate an/or isopropyl alcohol) are combined and thoroughly mixed together in a vessel.

The formulation is then transferred to a coating operation where it is coated onto a protective release liner at a controlled specified thickness. The coated product is then passed through an oven in order to drive off all volatile processing solvents.

The dried product on the release liner is then joined to the backing material and wound into rolls for storage.

Appropriate size and shape "systems" are die-cut from the roll material and then pouched.

Other manufacturing methods are known in the art that are suitable for making the systems described herein.

In some embodiments, there is provided a method of effecting transdermal drug delivery of levonorgestrel and ethinyl estradiol, by applying a system as described herein to the skin or mucosa of a subject in need thereof. In some embodiments, the system is applied over a period of at least about 1 day, at least about 2 days, at least about 3 days, at least about 4 days, at least about 5 days, at least about 6 days, or at least about 7 days, such as for 1, 2, 3, 4, 5, 6 or 7 days. In some embodiments, the method is effective to achieve therapeutic levels of levonorgestrel and ethinyl estradiol in the subject during the application period.

In some embodiments, the systems described herein are designed for use by female patients, such as for contraception.

The following specific examples are included as illustrative of the transdermal drug delivery systems and polymer matrices described herein. These examples are in no way intended to limit the scope of the invention. Other aspects of the invention will be apparent to those skilled in the art to which the invention pertains.

Example 1

A polymer matrix with the following composition is prepared:

| Ingredient | % w/w in Finished Dry Product |
|---|---|
| Acrylic polymer (Duro-Tak 87-2516) | 88.1 |
| Levonorgestrel | 1.4 |
| Ethinyl Estradiol | 0.5 |
| Glyceryl monooleate | 10 |
| Total | 100.00 |

The polymer matrix is applied to release liner and dried, a backing material is applied, and transdermal drug delivery systems of a suitable size are prepared Example 2

Figure 1:
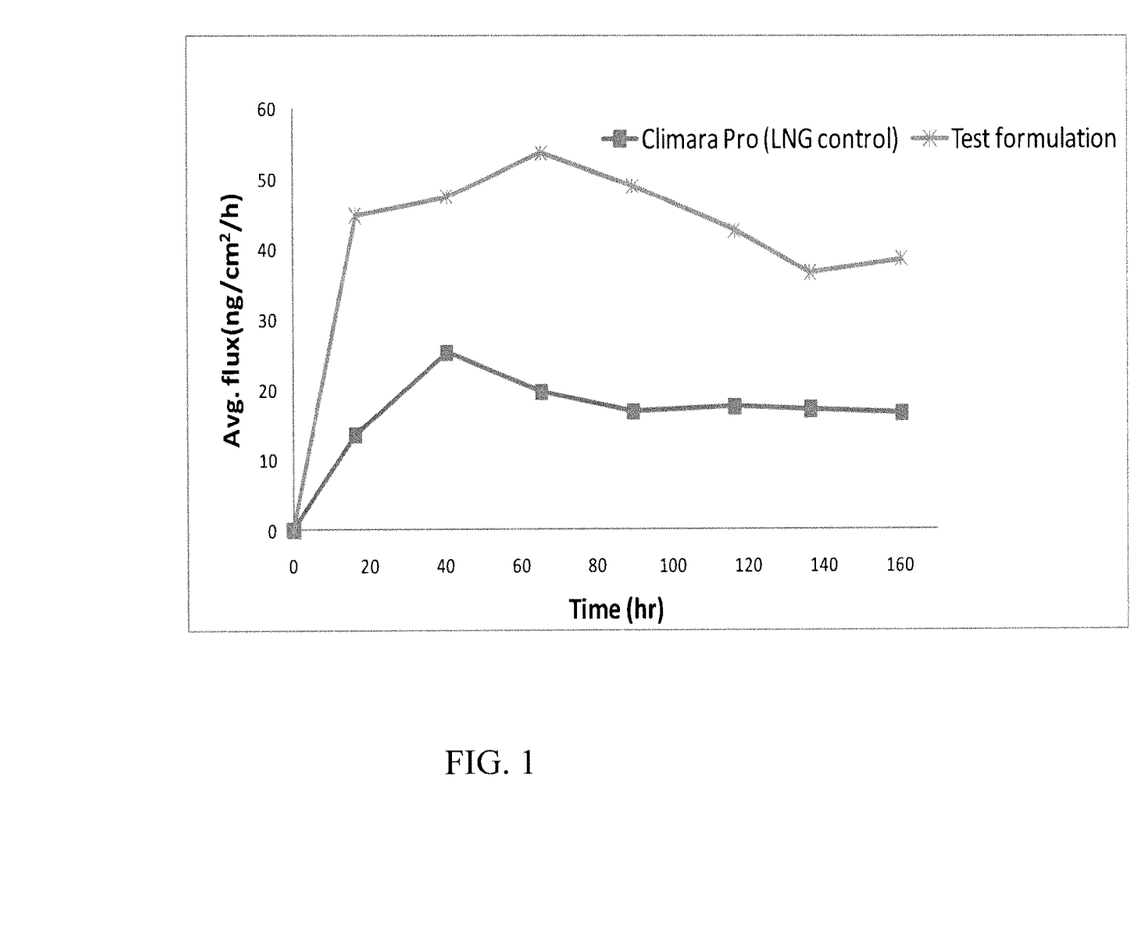
FIG. 1 illustrates the levonorgestrel flux ($\mu g/cm^2/hr$) over time (0-160 hours) from a transdermal delivery system according to the invention (-), as compared to Climara® Pro (■).
Figure 2:
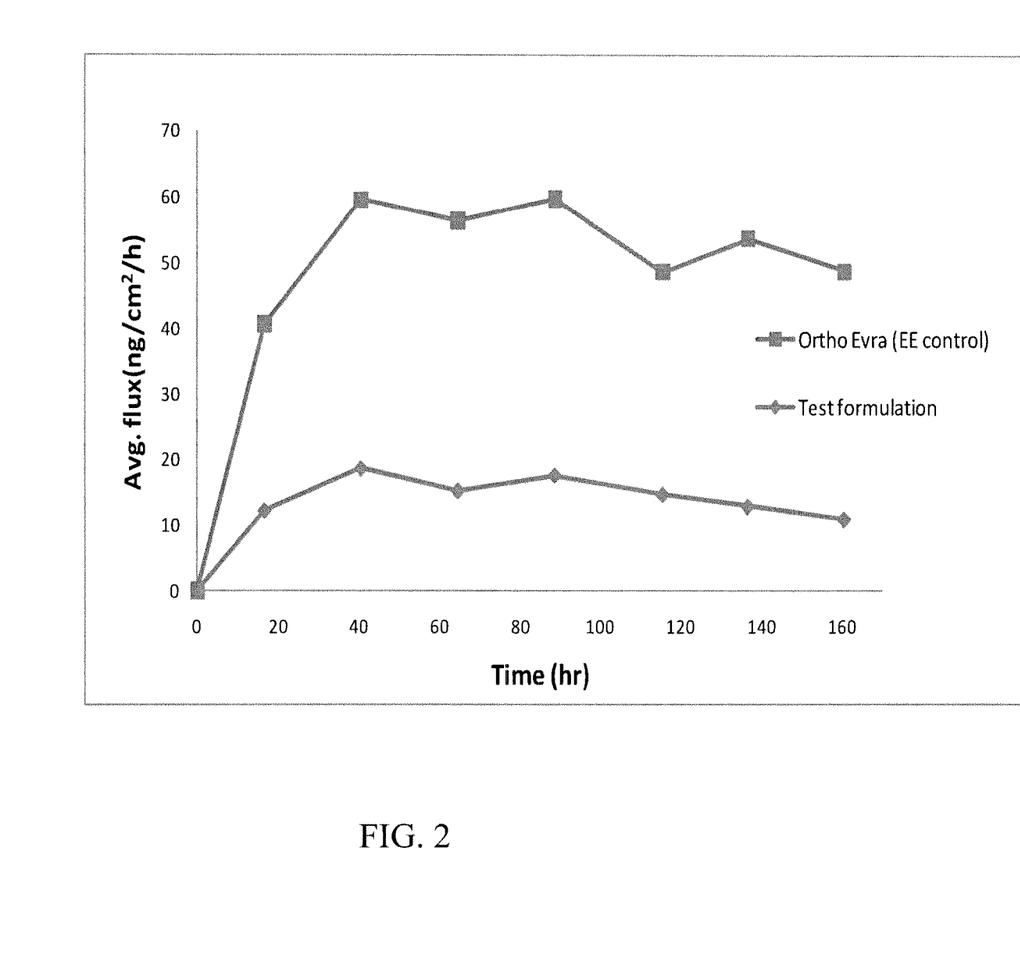
FIG. 2 illustrates the ethinyl estradiol flux ($\mu g/cm^2/hr$) over time (0-160 hours) from a transdermal delivery system according to the invention (♦), as compared to OrthoEvra® (■).

The polymer matrix of Example 1 was used to prepare transdermal drug delivery systems. An in vitro flux study was conducted with human cadaver skin using a Franz cell apparatus to determine the flux of each drug from the matrix over a 160-hour (~7 day) period, as compared to a corresponding commercial product. Results are shown FIGS. 1-2. FIG. 1 illustrates the levonorgestrel flux ($\mu g/cm^2/hr$) over time (0-160 hours) from a transdermal delivery system according to the invention (–), as compared to Climara® Pro (■). FIG. 2 illustrates the ethinyl estradiol flux ($\mu g/cm^2/hr$) over time (0-160 hours) from a transdermal delivery system according to the invention (♦), as compared to OrthoEvra® (■).

These data show that the systems described herein are able to achieve sustained delivery of levonorgestrel and ethinyl estradiol over an extended period of time of about 7 days.

Example 3

Polymer matrices with different relative amounts of ethinyl estradiol were prepared as follows.

| Ingredient | Sample 1 (♦) % w/w in Finished Dry Product | Sample 2 (▲) % w/w in Finished Dry Product | Sample 3 (-x-) % w/w in Finished Dry Product |
|---|---|---|---|
| Ethinyl Estradiol | 0.5 | 1 | 1.5 |
| Levonorgestrel | 2 | 2 | 2 |
| Kollidone VA 64 (PVP/VA) | 20 | 20 | 20 |
| Acrylic polymer (Duro-Tak 87-2516) | 67.5 | 67.5 | 67.5 |
| Glyceryl monooleate | 10 | 10 | 10 |
| Total | 100.00 | | |

Figure 3:
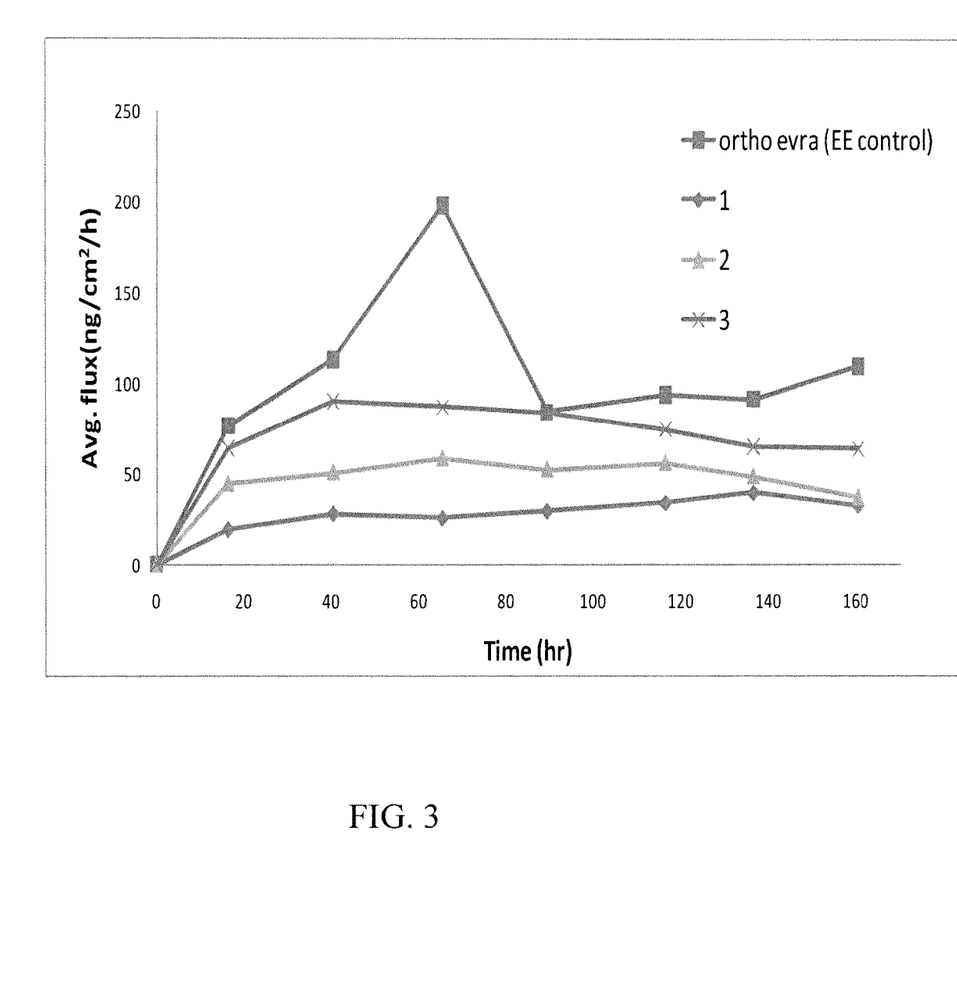
FIG. 3 illustrates the effect of ethinyl estradiol concentration on ethinyl estradiol flux ($\mu g/cm^2/hr$) over time (0-160 hours) from a transdermal delivery system according to the invention (♦, ▲, -×-), as compared to OrthoEvra® (■).

An in vitro flux study was conducted with human cadaver skin using a Franz cell apparatus to determine the flux of ethinyl estradiol from the matrices over a 160-hour (~7 day) period. Results are shown in FIG. 3 (♦, ▲, -x-), as compared to OrthoEvra® (■). These data show that the flux of ethinyl estradiol can be selected and controlled by selecting and controlling the amount of ethinyl estradiol in the polymer matrix.

What is claimed is:

1. A transdermal drug delivery system, for the transdermal delivery of levonorgestrel and ethinyl estradiol in the form of a flexible finite system for topical application, comprising a polymer matrix comprising (i) 0.1-3% levonorgestrel; (ii) 0.1-5% ethinyl estradiol; (iii) 5-20% of a penetration enhancer selected from the group consisting of glyceryl monooleate, dipropylene glycol, and mixtures thereof, and (iv) q.s. acrylic polymer, wherein the acrylic polymer comprises a hydroxy functional acrylic polymer, wherein the polymer matrix is free of polyvinylpyrrolidone (PVP) and polyvinylpyrrolidone/vinylacetate (PVP/VA) copolymer.

2. The transdermal drug delivery system of claim 1, further comprising a backing layer.

3. The transdermal drug delivery system of claim 2, wherein the transdermal drug delivery system is effective to achieve sustained delivery of levonorgestrel over a period of time selected from at least 3 days, at least 4 days, or at least 7 days.

4. The transdermal drug delivery system of claim 2, wherein the transdermal drug delivery system is effective to achieve sustained delivery of ethinyl estradiol over a period of time selected from at least 3 days, at least 4 days, or at least 7 days.

5. The transdermal drug delivery system of claim 1, further comprising a release liner.

6. A method of transdermally delivering levonorgestrel and ethinyl estradiol comprising applying a transdermal drug delivery system according to claim 1 to the skin or mucosa of a subject in need thereof.

7. The method of claim 6, wherein the subject is a human female subject.

8. The method of claim 7, wherein the method is for contraception.

9. The method of claim 6, wherein the transdermal drug delivery system is applied for a duration of up to 7 days.

10. A method of preparing a transdermal drug delivery system comprising levonorgestrel and ethinyl estradiol in the form of a flexible finite system for topical application, comprising preparing a polymer matrix comprising (i) 0.1-3% levonorgestrel, (ii) 0.1-5% ethinyl estradiol, (iii) a penetration enhancer selected from the group consisting of glyceryl monooleate, dipropylene glycol, and mixtures thereof, and (iv) q.s. acrylic polymer, wherein the acrylic polymer comprises a hydroxy functional acrylic polymer, wherein the polymer matrix is free of polyvinylpyrrolidone (PVP) and polyvinylpyrrolidone/vinylacetate (PVP/VA) copolymer.

11. The method of claim 10, wherein the polymer matrix consists of the 0.1-3% levonorgestrel; the 0.1-5% ethinyl estradiol; 5-20% of the penetration enhancer, and q.s. of the acrylic polymer.

* * * * *